US009855022B2

United States Patent
Christiansen et al.

(10) Patent No.: US 9,855,022 B2
(45) Date of Patent: Jan. 2, 2018

(54) 3-D FLOW ESTIMATION USING ROW-COLUMN ADDRESSED TRANSDUCER ARRAYS

(71) Applicant: B-K Medical APS, Herlev (DK)

(72) Inventors: Thomas Lehrmann Christiansen, Copenhagen (DK); Morten Fischer Rasmussen, Copenhagen (DK); Simon Holbek, Copenhagen (DK); Erik Vilain Thomsen, Lynge (DK); Jorgen Arendt Jensen, Horsholm (DK)

(73) Assignee: B-K Medical Aps, Herlev (DK)

( * ) Notice: Subject to any disclaimer, the term of this patent is extended or adjusted under 35 U.S.C. 154(b) by 347 days.

(21) Appl. No.: 14/599,857

(22) Filed: Jan. 19, 2015

(65) Prior Publication Data

US 2016/0206285 A1     Jul. 21, 2016

(51) Int. Cl.
*A61B 8/00* (2006.01)
*A61B 8/08* (2006.01)
(Continued)

(52) U.S. Cl.
CPC .............. *A61B 8/4483* (2013.01); *A61B 8/06* (2013.01); *A61B 8/483* (2013.01); *A61B 8/488* (2013.01);
(Continued)

(58) Field of Classification Search
CPC .... A61B 8/00; A61B 8/08; A61B 8/06; A61B 8/488; A61B 8/5207; A61B 8/5223
See application file for complete search history.

(56) References Cited

U.S. PATENT DOCUMENTS

| 5,840,032 A * | 11/1998 | Hatfield | A61B 8/06 |
| | | | 128/916 |
| 2003/0100832 A1* | 5/2003 | Criton | A61B 8/06 |
| | | | 600/443 |

(Continued)

FOREIGN PATENT DOCUMENTS

| WO | 9800719 | 1/1998 |
| WO | 0068678 | 11/2000 |

(Continued)

OTHER PUBLICATIONS

Christiansen, et al., Thomas Lehrmann, Row-column Addressed 2-D CMUT Arrays with Integrated Apodization, 13th International Workshop on Micromachined Ultrasonic Transducers, Kgs., Lyngby, Denmark, May 20, 2014.

(Continued)

*Primary Examiner* — Joel Lamprecht
(74) *Attorney, Agent, or Firm* — Anthony M. Del Zoppo, III; Driggs, Hogg, Daugherty & Del Zoppo Co. LPA (57) ABSTRACT

An ultrasound system includes a 2-D transducer array and a velocity processor. The 2-D transducer array includes a first 1-D array of one or more rows of transducing elements configured to produce first ultrasound data. The 2-D transducer array further includes a second 1-D array of one or more columns of transducing elements configured to produce second ultrasound data. The first and second 1-D arrays are configured for row-column addressing. The velocity processor processes the first and the second ultrasound data, producing 3-D vector flow data. The 3-D vector flow data includes an axial component, a first lateral component transverse to the axial component, and a second lateral component transverse to the axial component and the first lateral component.

32 Claims, 10 Drawing Sheets

(51) Int. Cl.
*A61B 8/06* (2006.01)
*G01S 15/89* (2006.01)
*A61B 8/14* (2006.01)

(52) U.S. Cl.
CPC ...... *G01S 15/8925* (2013.01); *G01S 15/8927* (2013.01); *G01S 15/8979* (2013.01); *A61B 8/14* (2013.01); *G01S 15/8993* (2013.01)

(56) References Cited

U.S. PATENT DOCUMENTS

| | | | | |
|---|---|---|---|---|
| 2013/0310679 | A1* | 11/2013 | Natarajan | A61B 8/445 600/411 |
| 2015/0087991 | A1* | 3/2015 | Chen | G01S 7/5202 600/459 |
| 2015/0099978 | A1* | 4/2015 | Davidsen | A61B 8/4483 600/459 |

FOREIGN PATENT DOCUMENTS

| | | |
|---|---|---|
| WO | 0068697 | 11/2000 |
| WO | 0068931 | 11/2000 |
| WO | 03029840 | 4/2003 |
| WO | WO2013054149 | 4/2013 |

OTHER PUBLICATIONS

Jensen, et al., A New Method for Estimation of Velocity Vectors, IEEE Transactions of Ultrasonics, Ferroelectrics, and Frequency Control, vol. 45, No. 3, May 1998.

Daft, et al., Elevationa Beam Profile Control with Bias Polarity Patterns Applied to Microfabricated Ultrasound Transducers, 2003 IEEE Ultrasonics Symposium—1578-1581.

Pihl, et all, In Vivo Three-Dimensional Velocity vector Imaging and Volumetric Flow Rate Measurements, 2013 IEEE International Ultrasonics Symposium.

* cited by examiner

3-D FLOW ESTIMATION USING ROW-COLUMN ADDRESSED TRANSDUCER ARRAYS

TECHNICAL FIELD

The following generally relates to ultrasound imaging and more particularly to 3-D flow estimation using row-column addressed transducer arrays.

BACKGROUND

For ultrasound velocity estimation, the oscillation of the pulsed ultrasound field has been used to estimate the axial velocity component of the structure of interest. The axial component is the component of the velocity vector in the direction of propagation of ultrasound energy from the ultrasound transducer array. Several methods have been proposed in the literature to estimate the lateral components of the velocity vector (perpendicular to the axial component). For 2-D imaging using 1-D transducer arrays, these include speckle tracking, directional beamforming, and transverse oscillation (TO). In directional beamforming, the received signals are focused along the flow direction for a given depth. The signals for two emissions are then cross-correlated, and the shift between them is found. This is a shift in spatial position of the scatterers, and dividing by the time between emissions, thus, directly gives the velocity magnitude. The angle between the emitted beam and the flow direction must be known before the beamformation can be done. The angle could, e.g., be found from the B-mode image as in conventional spectral velocity estimation.

For 2-D velocity vector estimation using the TO approach, an oscillation oriented transverse to that of the ultrasound pulse is introduced in the ultrasound field by applying the same transmit beam as used in conventional axial velocity estimation and adjusting the apodization of the receive aperture in such a way that the whole aperture resembles two point sources. Two point sources separated in space will give rise to two interfering fields, which creates the transverse oscillation. Using the Fraunhofer approximation, the relation between the lateral spatial wavelength and the apodization function is $\lambda_x = 2\lambda_z z_0/d$, where d is the distance between the two peaks in the apodization function, $z_0$ is a depth, and $\lambda_z$ is the axial wavelength. In axial velocity estimation, a Hilbert transform is performed to yield two 90° phase shifted signals; the in-phase signal and the quadrature signal. This enables the direction of the flow to be determined. The 90° phase shift in the transverse direction can be accomplished by having two parallel beamformers in receive. The two receive beams are steered, so that the transverse distance between each beam is $\lambda_x/4$, which corresponds to a 90° phase shift in space. Along with these two TO lines, a center line can be beamformed by a third beamformer for conventional axial velocity estimation.

For 3-D velocity vector estimation using the TO approach, 2-D transducer arrays are used to generate the TO field in both lateral dimensions allowing estimation of the velocity vector components in all three dimensions. 3-D velocity vector estimation using multiple crossed-beam ultrasound Doppler velocimetry and speckle tracking have also been proposed in the literature. There is an unresolved need for other approaches to 3-D velocity vector estimation that are applicable to arrays with a reduced number of connections, such as row-column addressed arrays.

SUMMARY

Aspects of the application address the above matters, and others.

In one aspect, an ultrasound system includes a 2-D transducer array and a velocity processor. The 2-D transducer array includes a first 1-D array of one or more rows of transducing elements configured to produce first ultrasound data. The 2-D transducer array further includes a second 1-D array of one or more columns of transducing elements configured to produce second ultrasound data. The first and second 1-D arrays are configured for row-column addressing. The velocity processor processes the first and the second ultrasound data, producing 3-D vector flow data. The 3-D vector flow data includes an axial component, a first lateral component transverse to the axial component, and a second lateral component transverse to the axial component and the first lateral component.

In another aspect, a method includes employing row-column addressing with an orthogonally disposed 1-D arrays of a 2-D transducer array to produce data for determining 3-D velocity components. The method further includes processing, with a velocity processor, the data to produce the 3-D velocity components, which includes at least two lateral components, one transverse to the axial component and the other transverse to the axial component and the one lateral component.

In another aspect, an ultrasound imaging system includes a pair of 1-D arrays oriented orthogonal to each other and row-column addressed. The ultrasound imaging system further includes processing components that process an output of the pair of 1-D arrays to estimate an axial and two lateral components using 2-D velocity vector estimator.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following describes an approach to estimate the axial component and both lateral components of the 3-D velocity vector with ultrasound imaging data acquired through row-column addressing of two orthogonally oriented 1-D transducer arrays.

Figure 1:
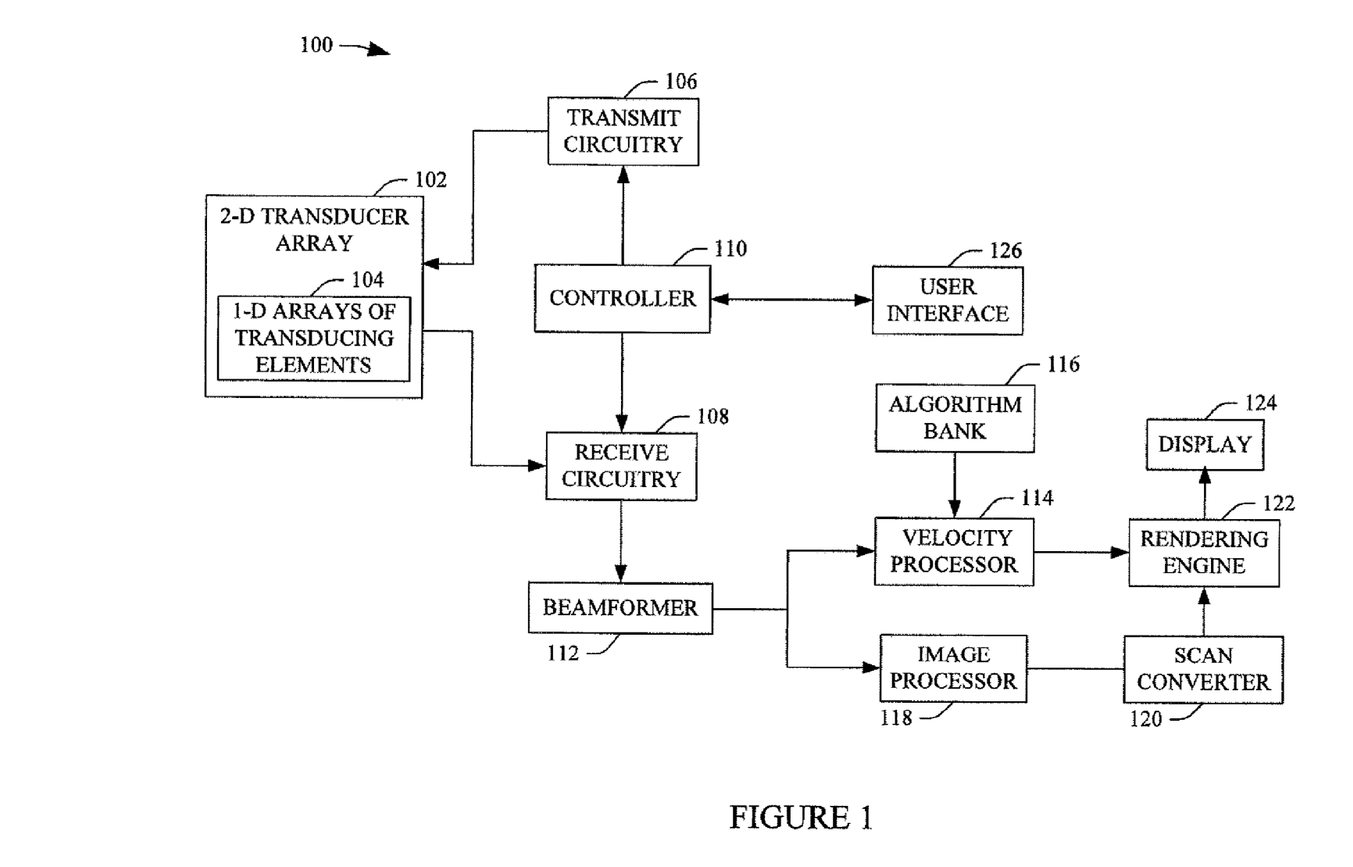
FIG. 1 schematically illustrates an example ultrasound imaging system with a 2-D transducer array of row-addressed orthogonal 1-D arrays.
Figure 2:
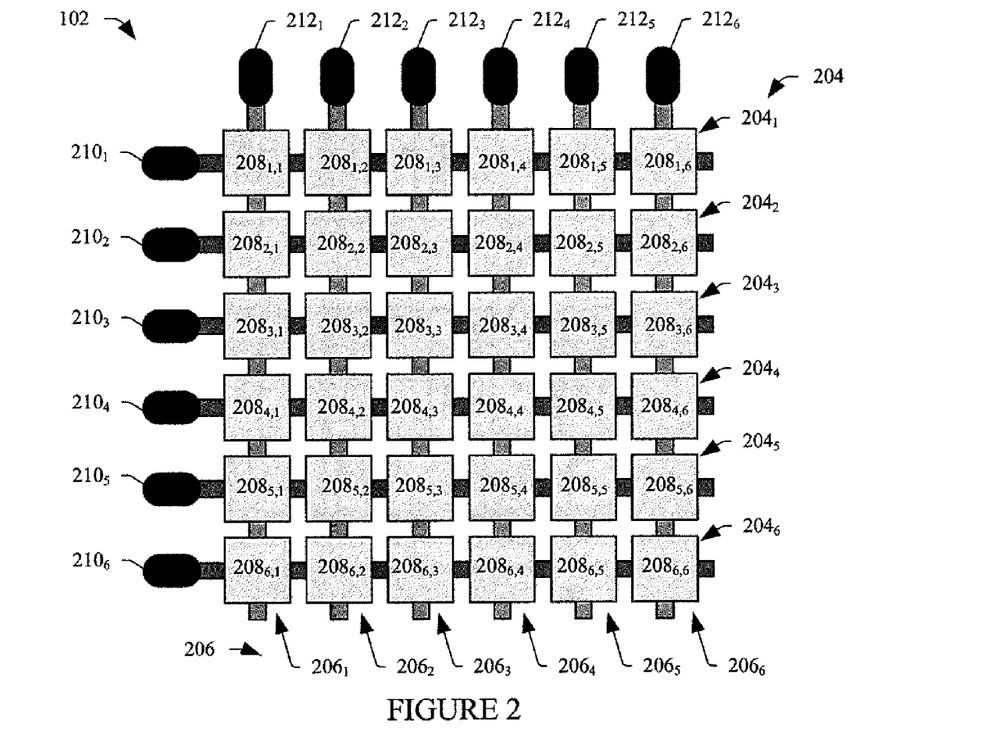
FIG. 2 schematically illustrates an example of the 2-D transducer array.

FIG. 1 schematically illustrates an example ultrasound imaging system 100. The ultrasound imaging system 100 includes a 2-D transducer array 102 with at least two one-dimensional (1-D) arrays 104 of transducing elements orthogonally arranged with respect to each other. An example of the 2-D array 102 includes N rows (or columns) and M columns (or rows) of transducing elements, where N and M are positive integers and N=M or N # M. The 2-D array 102 may include a 16×16, 32×32, 32×16, 64×64, larger or smaller array, a non-square/rectangular array, and/or other 2-D array. FIG. 2 illustrates an example of the 2-D transducer array 102.

Briefly turning to FIG. 2, the example 2-D transducer array 102 is 6×6 transducer array (N=M=6). The 2-D array 102 includes a plurality of rows $204_1$, $204_2$, $204_3$, $204_4$, $204_5$, and $204_6$, collectively referred to herein as rows 204. The 2-D array 102 also includes a plurality of columns $206_1$, $206_2$, $206_3$, $206_4$, $206_5$, and $206_6$, collectively referred to herein as columns 206. The rows 204 and columns 206 provide individual elements $208_{1,1}$, ..., $208_{1,6}$, ... $208_{6,1}$, ... $208_{6,6}$, collectively referred to herein as elements 208. The individual rows 204 and columns 206 are addressable (individually or in groups) respectively through contacts $210_1$, $210_2$, $210_3$, $210_4$, $210_5$, and $210_6$, and $212_1$, $212_2$, $212_3$, $212_4$, $212_5$, and $212_6$, collectively referred to as row contacts 210 and column contacts 212.

Returning to FIG. 1, multiple different types of row-column addressed array configurations are contemplated herein. One type includes a conventional row-column addressed 2-D array. This may allow volumetric imaging and estimation of all three velocity vector components in a volume. Another type includes a row-column addressed 2-D array with a physical or electronic elevation lens. This may offer two-way focused B-mode imaging and estimation of the two velocity vectors in the plane of the B-mode image in addition to the out-of-plane velocity vector. This transducer array may include a dynamic receive capability in elevation to improve B-mode image resolution.

The transducing elements may include piezoelectric, capacitive micromachined ultrasonic transducer (CMUT), and/or other transducing elements. Furthermore, the transducing elements may include integrated apodization, which may be identical or different for the individual elements. An example of integrated apodization is described in international patent application serial number PCT/IB2013/002838, entitled "Ultrasound Imaging Transducer Array with Integrated Apodization," and filed Dec. 19, 2013, the entirety of which is incorporated herein by reference. Furthermore, the 2-D array 102 may have a flat or a curved surface. Furthermore, the 2-D array 102 may include one or more lenses.

Transmit circuitry 106 generates pulses that excite a predetermined set of addressed 1D arrays of the 2-D array 102 to emit one or more ultrasound beams or waves into a scan field of view. Receive circuitry 108 receives echoes or reflected waves, which are generated in response to the transmitted ultrasound beam or wave interacting with (stationary and/or flowing) structure in the scan field of view, from a predetermined set of addressed arrays of the 2-D array 102. A controller 110 controls the transmit circuitry 106 and/or the receive circuitry 108 based on a mode of operation. An example of suitable control includes row-column addressing, as well as individual element addressing.

A beamformer 112 processes the echoes, for example, by applying time delays, weighting on the channels, summing, and/or otherwise beamforming received echoes. The beamformer 112 includes a plurality of beamformers (e.g., 2, 3, 4, 5, etc.) that process the echoes and produce data for determining the 3-D velocity components. As described in greater detail below, in one instance the beamformers simultaneously process the echoes, and, in another instance, the beamformers sequentially process the echoes. The illustrated beamformer 112 also produces data for generating images in A-mode, B-mode, Doppler, and/or other ultrasound imaging modes.

A velocity processor 114 processes the beamformed data to determine the 3-D velocity components. The velocity processor 114 employs on one or more algorithms from an algorithm bank 116. A suitable algorithm includes a 2-D velocity vector estimator such as a speckle tracking, crossed-beam ultrasound Doppler velocimetry, directional beamforming, transverse oscillation (TO), and/or other estimator. An image processor 118 also processes the beamformed data. For B-mode, this includes generating a sequence of focused, coherent echo samples along focused scanlines of a scanplane. The image processor 118 may also be configured to process the scanlines to lower speckle and/or improve specular reflector delineation via spatial compounding, apply filtering such as FIR and/or IIR, etc.

A scan converter 120 scan converts the output of the image processor 118 and generates data for display, for example, by converting the data to the coordinate system of the display. The scan converter 120 can be configured to employ analog and/or digital scan converting techniques. A rendering engine 122 visually presents one or more images and/or velocity information via a display monitor 124. Such presentation can be in an interactive graphical user interface (GUI), which allows the user to selectively rotate, scale, and/or manipulate the displayed data. Such interaction can be through a mouse or the like, and/or a keyboard or the like, and/or other approach for interacting with the GUI.

A user interface 126 includes one or more input devices (e.g., a button, a knob, a slider, a touch pad, etc.) and/or one or more output devices (e.g., a display screen, lights, a speaker, etc.). A particular mode, scanning, and/or other function can be activated by one or more signals indicative of input from the user interface 126. For example, where the algorithm bank 116 include more than one 2-D velocity vector estimators the user interface 126 can be used to select one through a user input. The user interface 126 can also be used to set and/or change parameters such as imaging parameters, processing parameters, display parameters, etc.

The beamformer 112, the velocity processor 114 and/or the image processor 118 can be implemented via a processor (e.g., a microprocessor, a CPU, a GPU, etc.) executing one or more computer readable instructions encoded or embedded on non-transitory computer readable storage medium such as physical memory. Such a processor can be part of the system 100 and/or a computing device remote from the system 100. Additionally or alternatively, the processor can execute at least one computer readable instructions carried by a carrier wave, a signal, or other transitory medium.

In one instance, the transducer array 102 is part of a probe and the transmit circuitry 106, the receive circuitry 108, the beamformer 112, the controller 110, the velocity processor 114, the image processor 118, the scan converter 120, the rendering engine 122, the user interface 126, and the display 124 are part of a separate console. Communication there between can be through a wired (e.g., a cable and electromechanical interfaces) and/or wireless communication channel. In this instance, console can be similar to a portable computer such as a laptop, a notebook, etc., with additional hardware and/or software for ultrasound imaging. The console can be docked to a docketing station and used.

Alternatively, the console can be part (fixed or removable) of a mobile or portable cart system with wheels, casters, rollers, or the like, which can be moved around. In this instance, the display 124 may be separate from the console and connected thereto through a wired and/or wireless communication channel. Where the cart includes a docking interface, the laptop or notebook computer type console can be interfaced with the cart and used. An example of a cart system where the console can be selectively installed and removed is described in US publication 2011/0118562 A1, entitled "Portable ultrasound scanner," and filed on Nov. 17, 2009, which is incorporated herein in its entirety by reference.

Alternatively, the transducer array 102, the transmit circuitry 106, the receive circuitry 108, the beamformer 112, the controller 110, the velocity processor 114, the image processor 118, the scan converter 120, the rendering engine 122, the user interface 126, and the display 124 are housed within a hand-held ultrasound apparatus, where the housing mechanically supports and/or encloses the components therein. In this instance, the transducer array 102 and/or the display 124 can be part of the housing, being structurally integrated or part of a surface or end of the hand-held ultrasound apparatus. An example of a hand-held device is described in U.S. Pat. No. 7,699,776, entitled "Intuitive Ultrasonic Imaging System and Related Method Thereof," and filed on Mar. 6, 2003, which is incorporated herein in its entirety by reference.

Figure 3:
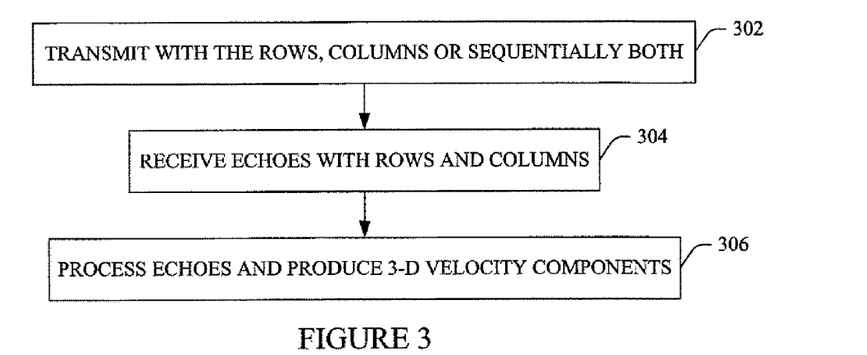
FIG. 3 illustrates an example method for determining 3-D vector velocity component utilizing the 2-D transducer array of row-addressed orthogonal 1-D arrays.

FIG. 3 illustrates a method for 3-D flow estimation using row-column addressed arrays.

At 302, either the rows or the columns (or both sequentially) are used as transmit elements. Any apodization and phase delay can be applied to the transmit elements, and any number of transmit elements can be used simultaneously. Furthermore, any emission technique may be used, e.g. focused emission, plane wave emission, single element emission, synthetic transmit aperture, etc.

Figure 4:
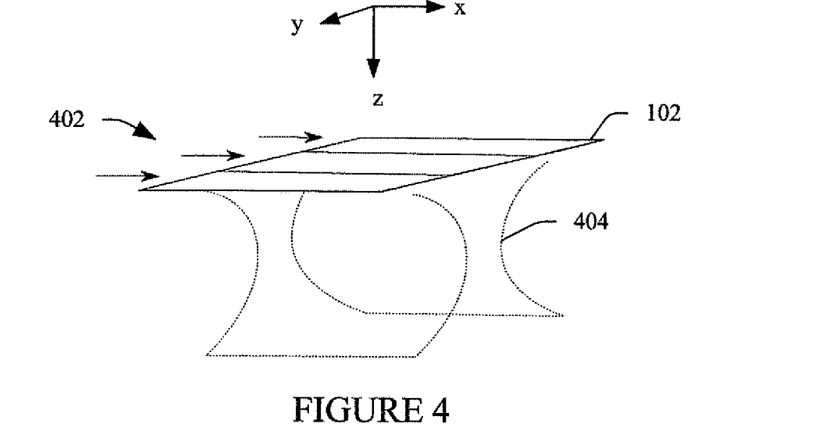
FIGS. 4 and 5 schematically illustrate transmit along rows (or columns) and receive by both rows and columns.

An example of transmit along a subset of the rows or the columns 402 of the 2-D transducer array 102 is shown in FIG. 4. In FIG. 4, the example transmit produces a focused sound wave 404 in one line of direction.

Figure 5:
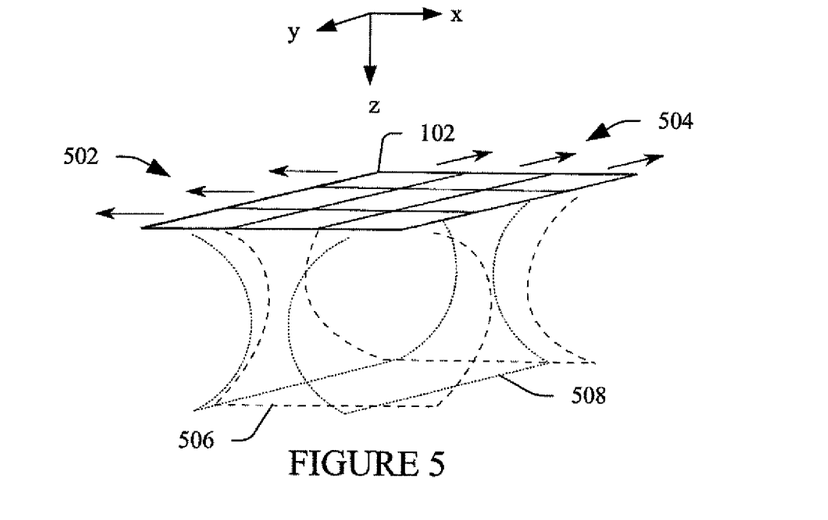

Returning to FIG. 3, at 304, echoes are subsequently received by the rows and the columns. An example of this is shown in FIG. 5, which shows both rows 502 (or columns) and columns 504 (or rows) of the 2-D transducer array 102 respectively receive echoes 506 and 508.

Returning to FIG. 3, at 306, the echoes are processed to determine the 3-D velocity components. Depending on the velocity estimator, any subset of the received signals may be used. For example, in one instance, only the signals received by the rows are used. Furthermore, any apodization and phase delay may be applied to the receiving elements. The full 3-D velocity estimation may be performed using a single or several of such transmit-receive events, which may be combined in the estimation.

Figure 6:
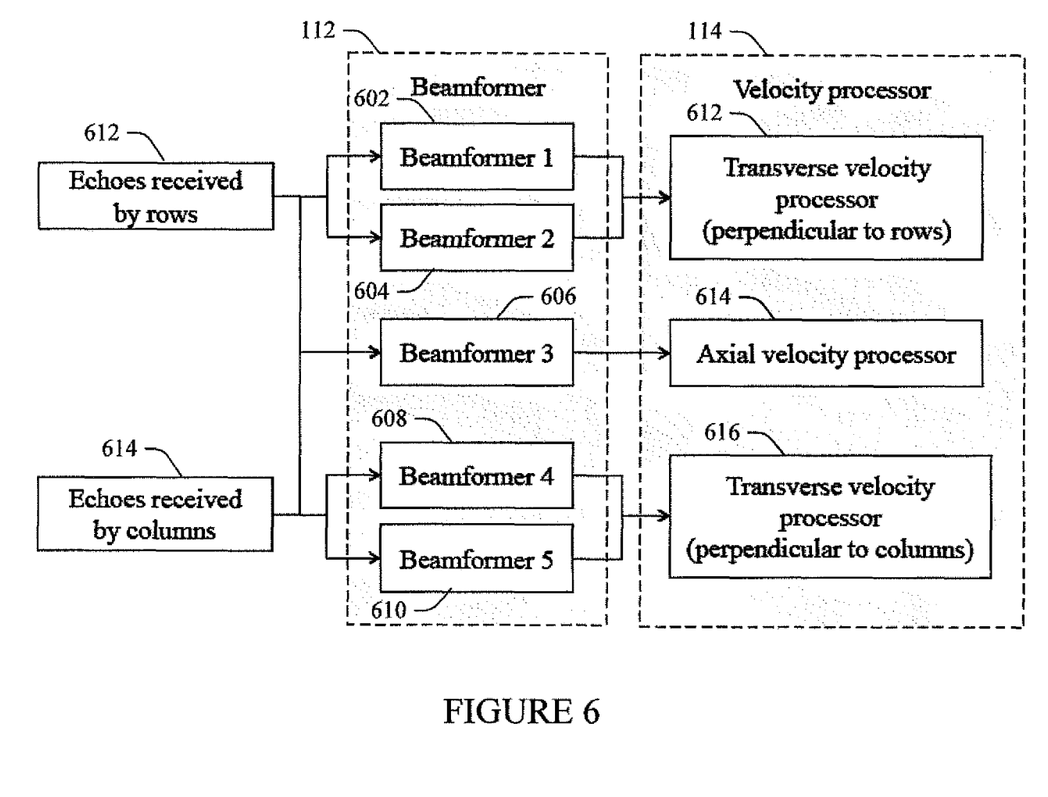
FIG. 6 schematically illustrates an example beamformer and velocity processor.

In one embodiment, the controller 110 controls the transmit circuitry 106 so that either the rows or the columns emit ultrasound, and the velocity processor 114 estimates velocity by synthesizing TO fields in receive for both the rows and columns, respectively. The sequence may be repeated with the same or different transmit setup. This embodiment may be realized with a total of five beamformers 602, 604, 606, 608 and 610, as shown in FIG. 6, each beamforming a line. The velocity processor 114 includes a transverse velocity processor 612, a transverse velocity processor 614, and an axial velocity processor 616.

The received signals from the rows 612 are processed by beamformers 602 and 604, which are configured to produce data, which the transverse velocity processor 612 processes to determine the velocity component perpendicular to the rows. The received signals from the columns 614 are processed by beamformers 608 and 610, which are configured to produce data, which the transverse velocity processor 614 processes to determine the velocity component perpendicular to the columns. Example approaches for each of the two sets of beamformers are described in Jensen et al., "A new method for estimation of velocity vectors," IEEE Trans. Ultrason., Ferroelec., Freq. Contr., vol. 45, pp. 837-851, 1998, Jensen, "A New Estimator for Vector Velocity Estimation", IEEE Trans. Ultrason., Ferroelec., Freq. Contr., vol. 48, pp. 886-894, 2001, and Udesen et al., "Investigation of Transverse Oscillation Method," IEEE Trans. Ultrason., Ferroelec., Freq. Contr., vol. 53, pp. 959-971, 2006, and international application publication WO/2000/068678, entitled "Estimation of Vector Velocity," and filed Nov. 16, 2000, the entirety of which is incorporated herein by reference.

Figure 7:
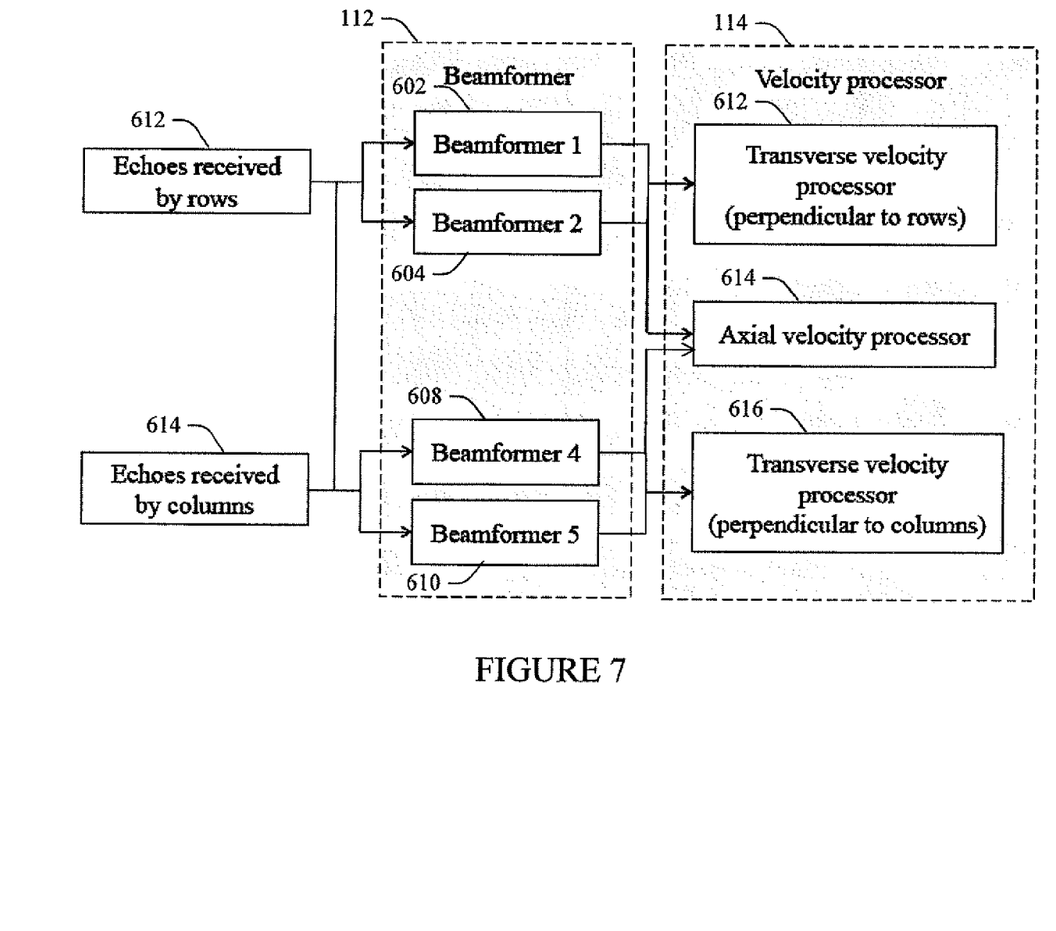
FIG. 7 schematically illustrates a variation of the beamformer of FIG. 6.

The beamformer 606 is configured to produce data, which the axial velocity processor 616 processes to determine the axial velocity component. In one instance, the beamformer 606 processes the signals received by the rows 612. In another instance, the beamformer 606 processes the signals received by the columns 614. In yet another instance, the beamformer 606 processes both the signals received by the rows 612 and the signals received by columns 614. In a variation, the beamformer 606 is omitted, and data from beamformers 602 and 604 and/or the beamformers 608 and 610 are feed to the axial velocity processor 616, as shown in FIG. 7, which processes the signals to determine the axial velocity component.

Figure 8:
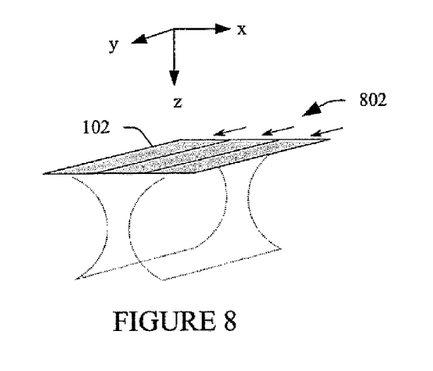
FIGS. 8, 9, 10 and 11 schematically illustrate transmit along rows (or columns) and receive along columns (or rows), and subsequent transmit along columns (or rows) and receive along rows (or columns)
Figure 9:
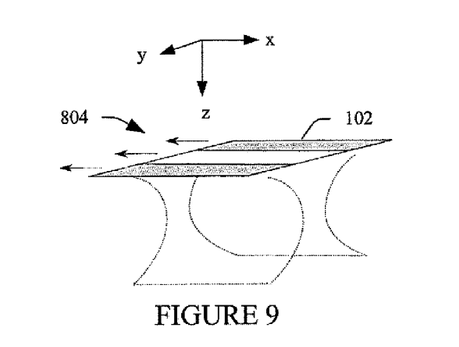
Figure 10:
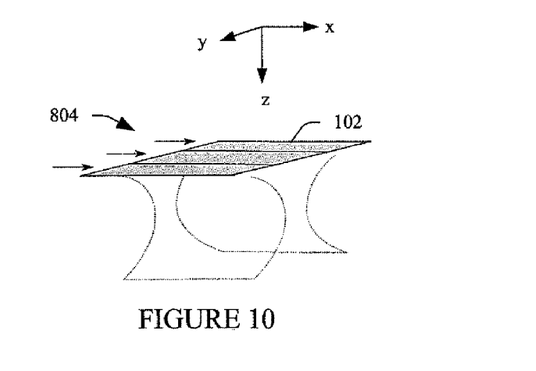
Figure 11:
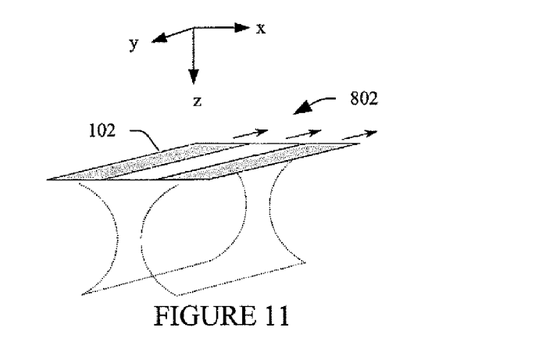

In a variation, columns 802 (or rows 804) emit ultrasound (FIG. 8), and the TO field is synthesized in receive using the rows 804 (or the columns 802) (FIG. 9). This allows estimation of the velocity component perpendicular to the rows (or columns). Subsequently, the rows 804 (or the columns 802) emit ultrasound (FIG. 10), and the TO field is synthesized in receive using the columns 802 (or the rows 804) (FIG. 11). This allows estimation of the velocity component perpendicular to the columns (or rows). The axial velocity component may be estimated using data from either of the two transmit-receive events. The signal processing may be done as shown in FIG. 6.

Figure 12:
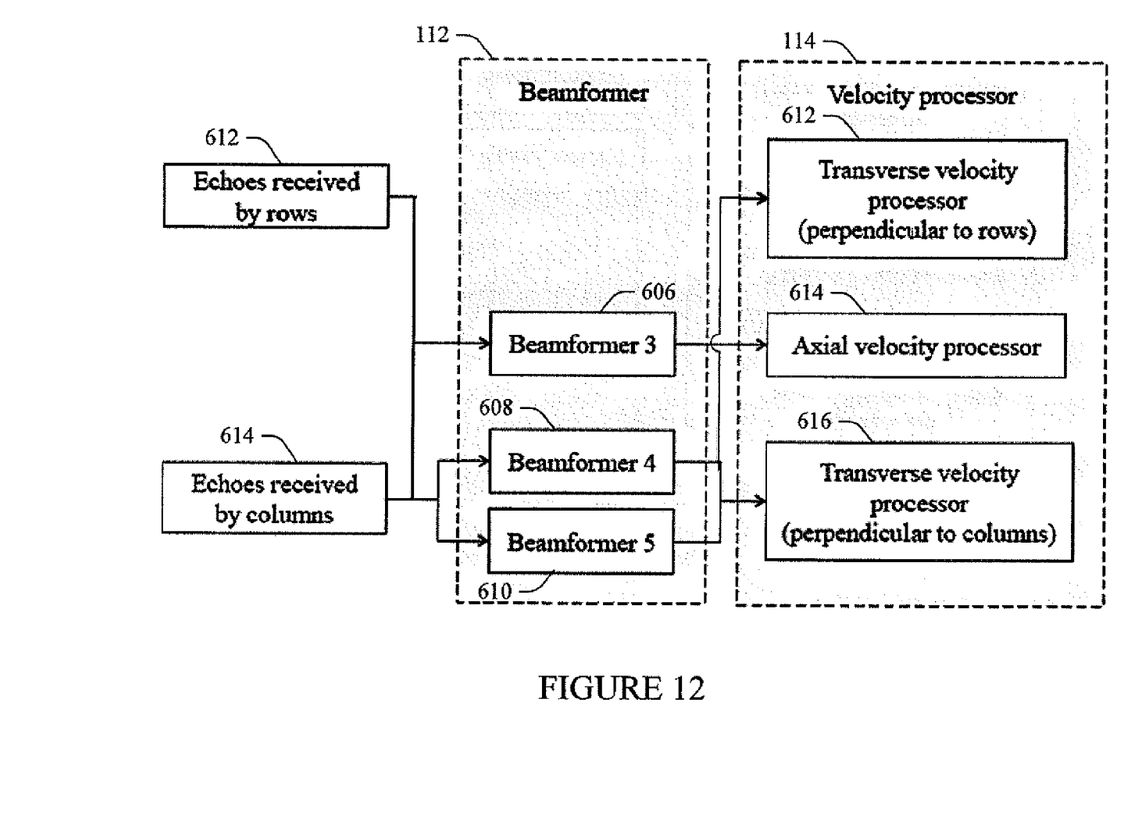
FIGS. 12 and 13 schematically illustrate other variations of the beamformer of FIG. 6.
Figure 13:
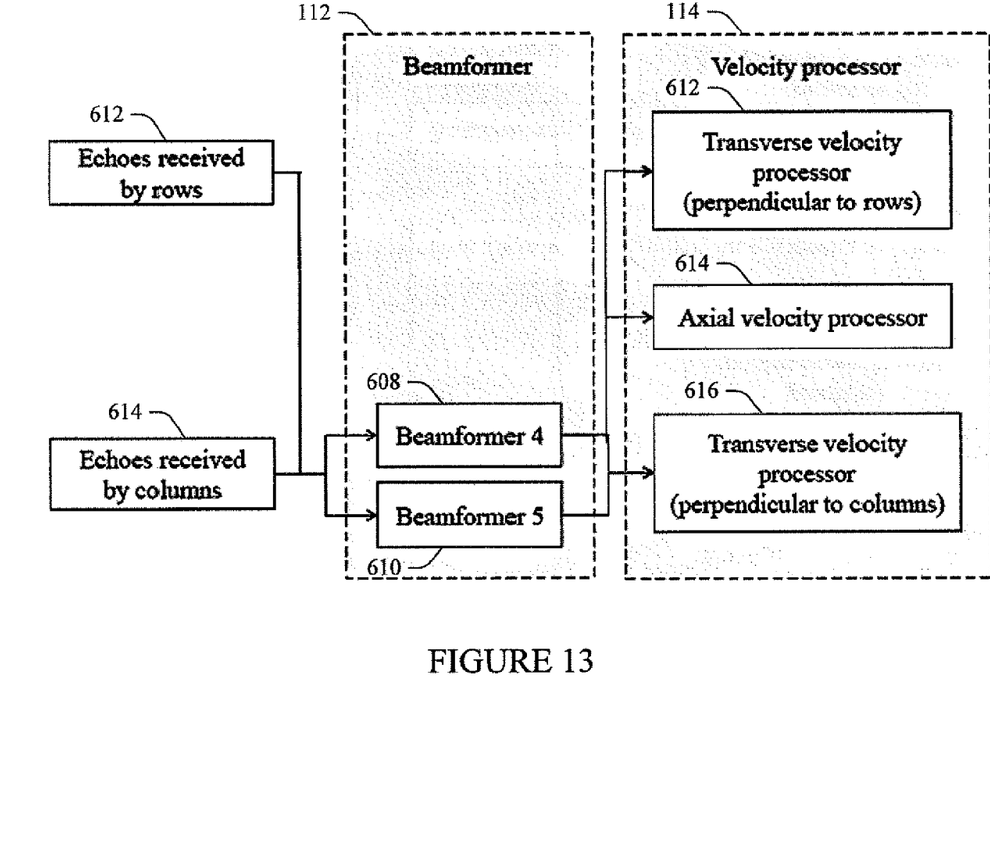

Alternatively, the signal processing may be done as shown in FIG. 12. FIG. 12 is substantially similar to FIG. 6 except that the two of beamformers feeding one the transverse velocity processors are omitted. In this example, the beamformer 602 and 604, are omitted. In another example, the beamformers 608 and 610, are omitted. This can be implemented because the two transverse components of the velocity vector are estimated in two separate transmit-receive events. Hence, the same set of beamformers may be used. In a variation, the axial beamformer 606 is also omitted (FIG. 13), and data from beamformers 602 and 604 and/or beamformer 608 and 610 (as shown) is used to feed the axial velocity processor 614.

In another embodiment, either the rows or columns emit ultrasound, and the velocity estimation is subsequently done by performing directional beamforming in receive for both the rows and columns, respectively. The sequence may be repeated with the same or different transmit setup. In another embodiment, the rows emit ultrasound, and the velocity estimation is done by performing directional beamforming in receive for the columns. This is used to estimate the velocity component perpendicular to the columns. Subsequently, the columns emit ultrasound, and the velocity estimation is done by performing directional beamforming in receive for the rows. This is used to estimate the velocity component perpendicular to the rows. In both embodiments using directional beamforming, two angles must be predetermined.

Figure 14:
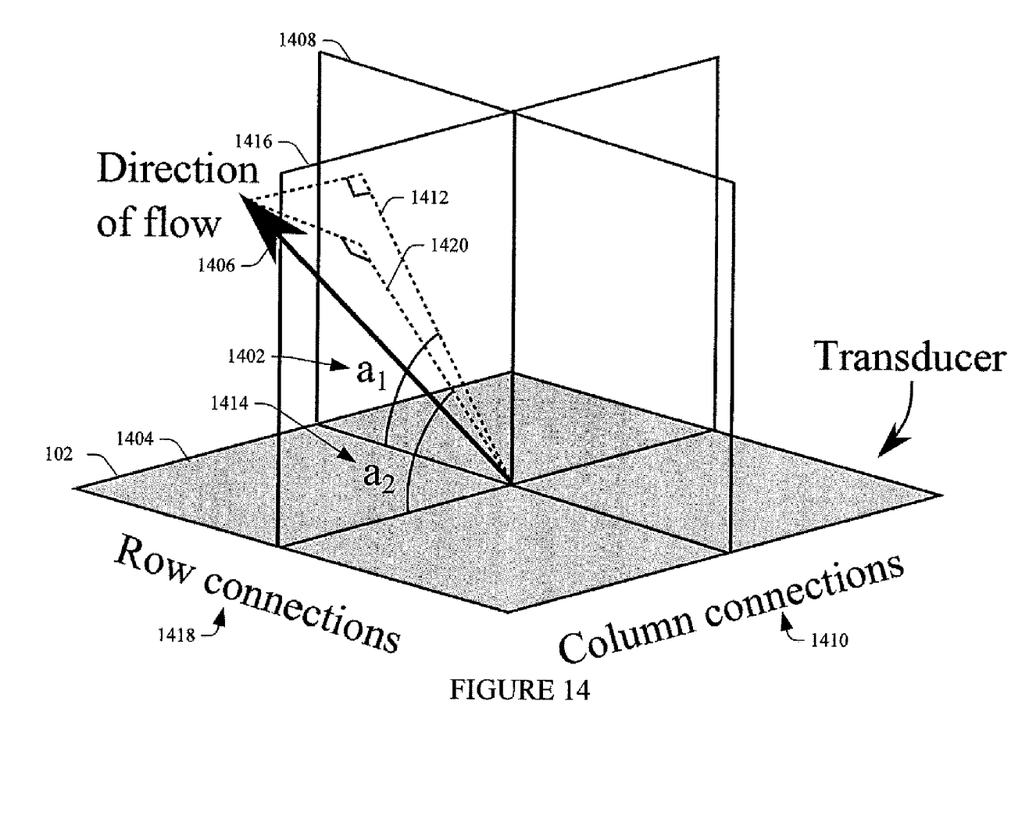
FIG. 14 shows an example of the two angles used for a velocity estimator using directional beamforming.

As shown in FIG. 14, this includes a first angle (a1) 1402 between a surface 1404 of the transducer array 102 and a first projected direction of flow 1412, which is a direction of flow 1406 projected on a plane 1408 parallel to columns 1410. This also includes a second angle (a2) 1414 between the transducer surface 1404 and a second projected direction of flow 1420, which is the direction of flow 1406 projected on a plane 1416 parallel to columns 1418. These angles are used to determine the line to be produced using the received data. They may be estimated e.g. from the volumetric image generated by the transducer array. Alternatively, they may be found using the TO approach and/or the methods approach disclosed in Jensen et al., "Estimation of velocity vectors in synthetic aperture ultrasound imaging." IEEE Trans. Ultrason., Ferroelec., Freq. Contr., vol. 25, pp. 1637-1644, 2006, Kortbek et al., "Estimation of velocity vector angles using the directional cross-correlation method," IEEE Trans. Ultrason., Ferroelec., Freq. Contr., vol. 53, pp. 2036-2049, 2006, and/or other approach.

Figure 15:
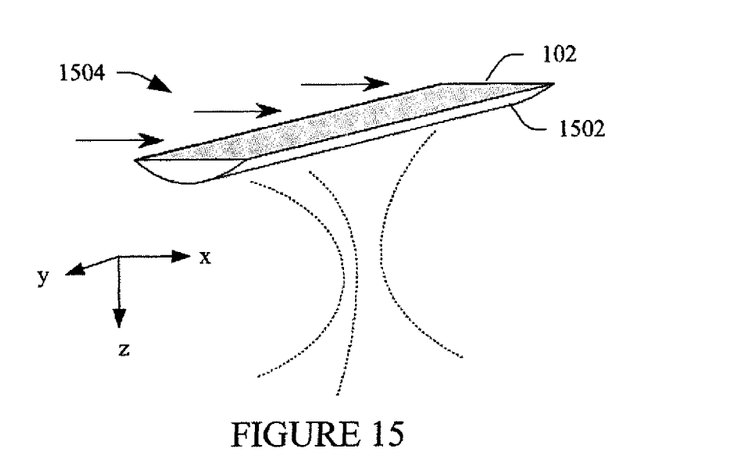
FIGS. 15, 16 and 17 illustrate an example in which the 2-D array 102 includes a physical lens for fixed elevation focus.
Figure 16:
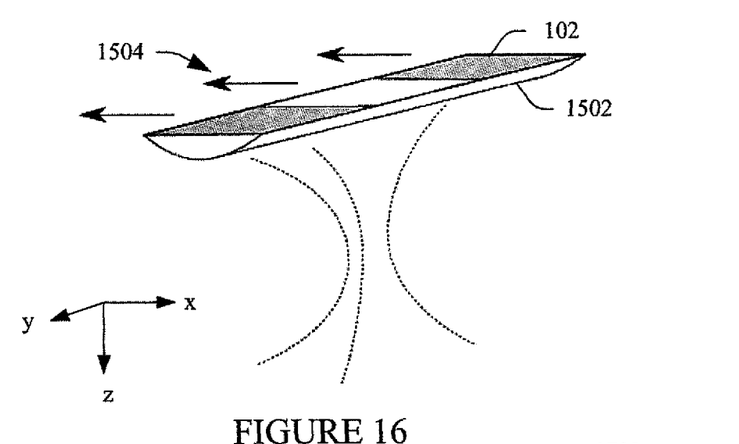
Figure 17:
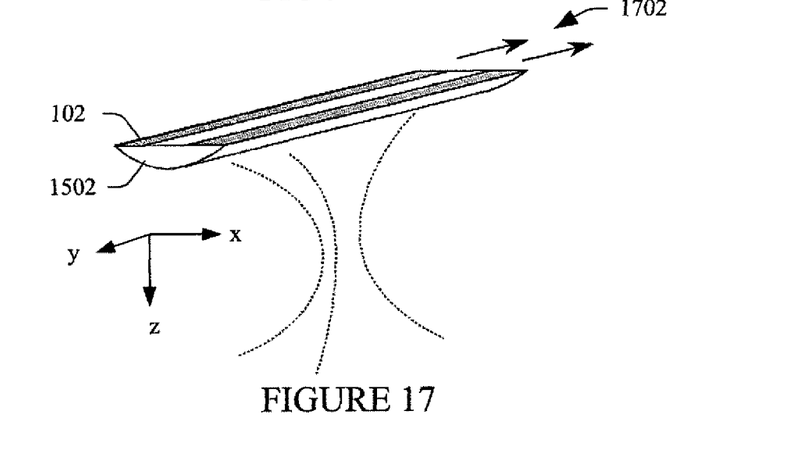

FIGS. 15, 16 and 17 illustrate an example in which the 2-D array 102 includes a physical lens 1502 giving fixed elevation focus. A conventional row-column addressed array using delay-and-sum beamforming can only achieve one-way focusing in each dimension. The elevation lens 1502 can be of any suitable material and can focus in any desired depth. Alternatively, an electronic lens could be used. An example of an electronic lens is described in Daft et al., "Elevation beam profile control with bias polarity patterns applied to microfabricated ultrasound transducers," in Proc. IEEE Ultrason. Symp., vol. 2, 2003, pp. 1578-1581. In such a lens configuration, the row-column array essentially functions as a conventional 1-D array.

From FIG. 15, in the illustrated example rows 1504 oriented in the x-direction are used for transmitting. Electronic transmit focusing can then be performed in the y-direction, while the lens provides transmit focusing in the x-direction. A B-mode image can be acquired using the rows as receivers, in which case the array functions exactly like a 1-D array with elevation focus. The array may be used for estimating the 3-D velocity vector in the plane defined by the elevation lens. This is done by processing the data received on the rows and columns using an estimator discussed herein and/or other estimator for the conventional row-column addressed array.

The velocity vector component in the y-direction is estimated using received data from the rows 1504 (FIG. 16) and the velocity vector component in the x-direction is estimated using received data from columns 1702 (FIG. 17). The z-component may be estimated using received data from either the rows or the columns, e.g., as shown in FIG. 6. As such, by installing the lens 1502 on the row-column array, a two-way focused B-mode image with full 3-D velocity vector information in the plane of the B-mode image is achieved. This can be used for finding e.g. flow rate, direction of flow, peak velocities, etc., without sacrificing frame-rate nor B-mode image quality. A clinician will experience the same performance as when using a 1-D transducer for B-mode imaging in conjunction with 2-D velocity vector imaging, but with the addition of out-of plane velocity estimation.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound system, comprising:
a 2-D transducer array, including:
 a first 1-D array of one or more rows of transducing elements configured to produce first ultrasound data; and
 a second 1-D array of one or more columns of transducing elements (208) configured to produce second ultrasound data,
wherein the first and second 1-D arrays are configured for row-column addressing; and
a velocity processor that processes the first and the second ultrasound data, producing 3-D vector flow data, including: an axial component, a first lateral component transverse to the axial component, and a second lateral component transverse to the axial component and the first lateral component.

2. The ultrasound system of claim 1, further comprising:
an algorithm bank that includes at least one algorithm from a group consisting of speckle tracking, crossed-beam ultrasound Doppler velocimetry, directional beamforming and transverse oscillation,
wherein the velocity processor employs the at least one algorithm to process the first and the second ultrasound data to produce the 3-D vector flow data.

3. The ultrasound system of claim 1, further comprising:
transmit circuitry;
receive circuitry; and
 a controller that controls the transmit and receive circuitry to transmit using one of the first or second 1-D arrays and receive simultaneously from both of the first and second 1-D arrays.

4. The ultrasound system of claim 3, further comprising:
first and second beamformer that process signals from one of the first or second 1-D arrays and produce first beamformed data;
a first velocity processor that processes the first beamformed data, producing the velocity component perpendicular to the first or second 1-D array;
third and fourth beamformers that process signals from the other of the first or second 1-D arrays and produce second beamformed data; and
a second velocity processor that processes the second beamformed data, producing the velocity component perpendicular to the other of the first or second 1-D array.

5. The ultrasound system of claim 4, further comprising:
a fifth beamformer that process at least one of the signal from the first or the second 1-D array and produces third beamformed data; and
a third velocity processor that processes the third beamformed data, producing the axial component.

6. The ultrasound system of claim 4, further comprising:
a third velocity processor that processes at least one of first beamformed data or the second beamformed data, producing the axial component.

7. The ultrasound system of claim 1, further comprising:
transmit circuitry;
receive circuitry; and
 a controller that controls the receive and transmit circuitry to transmit using one of the first or second 1-D arrays and receive using the other of the first or second 1-D arrays and subsequently to transmit using the other of the first or second 1-D arrays and receive using the one of the first or second 1-D arrays, wherein the velocity processor processes data from at least one of transmit-receive sequences to estimate the lateral velocity components.

8. The ultrasound system of claim 7, further comprising:
first and second beamformer that process signals from one of the first or second 1-D arrays and produce first beamformed data;
a first velocity processor that processes the first beamformed data, producing the velocity component perpendicular to the first or second 1-D array;
third and fourth beamformer that process signals from the other of the first or second 1-D arrays and produce second beamformed data; and
a second velocity processor that processes the second beamformed data, producing the velocity component perpendicular to the other of the first or second 1-D array, wherein the first, second, third and fourth beamformers are different beamformers.

9. The ultrasound system of claim 8, further comprising:
a fifth beamformer that process at least one of the signal from the first or the second 1-D array and produces third beamformed data; and
a third velocity processor that processes the third beamformed data, producing the axial component.

10. The ultrasound system of claim 8, further comprising:
a third velocity processor that processes at least one of first beamformed data or the second beamformed data, producing the axial component.

11. The ultrasound system of claim 7, further comprising:
a first pair of beamformers that processes signals from one of the first or second 1-D arrays and produces first or second beamformed data;
a first velocity processor that processes the first beamformed data, producing the two lateral velocity components.

12. The ultrasound system of claim 11, further comprising:
an axial velocity beamformer that process at least one of the signal from the first or the second 1-D array and produces third beamformed data; and
a third velocity processor that processes the third beamformed data, producing the axial component.

13. The ultrasound system of claim 11, further comprising:
a third velocity processor that processes at least one of first beamformed data or the second beamformed data, producing the axial component.

14. The ultrasound system of claim 1, wherein the velocity processor employs transverse oscillation to produce the first and second lateral components.

15. The ultrasound system of claim 1, wherein the velocity processor employs directional beamforming to produce the first and second lateral components.

16. The ultrasound system of claim 1, further comprising:
an acoustical elevation lens affixed to the first and second 1-D arrays.

17. The ultrasound system claim 16, wherein the 2-D array is configured for two way focused B-Mode imaging, and the velocity processor estimates two velocity vectors in a plane of a B-mode image and a velocity vector out of the plane of the B-mode image.

18. A method, comprising:
employing row-column addressing with a orthogonally disposed 1-D arrays of a 2-D transducer array to produce data for determining 3-D velocity components; and
processing, with a velocity processor, the data to produce the 3-D velocity components, which includes at least two lateral components, one transverse to the axial component and the other transverse to the axial component and the one lateral component.

19. The method of claim 18, wherein the velocity processor employs at least one of speckle tracking, crossed-beam ultrasound Doppler velocimetry, directional beamforming and transverse oscillation to produce the 3-D velocity components.

20. The method of claim 19, further comprising:
transmitting ultrasound with only one of the orthogonally disposed 1-D arrays;
receiving echoes concurrently with the orthogonally disposed 1-D arrays; and
processing the received echoes to produce at least the two lateral components.

21. The method of claim 19, further comprising:
transmitting ultrasound with only one of the orthogonally disposed 1-D arrays and receiving echoes with only the other of the orthogonally disposed 1-D arrays; and
processing the received echoes to produce at least the two lateral components.

22. The method of claim 21, further comprising:
transmitting ultrasound with only the other of the orthogonally disposed 1-D arrays and receiving echoes with only the one of the orthogonally disposed 1-D arrays; and
processing the echoes received by the one and the other one of the 1-D arrays to produce at least the two lateral components.

23. The method of claim 18, further comprising:
applying apodization for the transmitting.

24. The method of claim 23, wherein the apodization is integrated into transducer elements of the 1-D arrays.

25. The method of claim 18, further comprising:
applying a phase delay for the transmitting.

26. The method of claim 18, further comprising:
utilizing at least one of focused emission, plane wave emission, single element emission, or synthetic transmit aperture for transmitting.

27. The method of claim 18, further comprising:
providing one-way focusing in both lateral directions.

28. The method of claim 18, further comprising:
employing a lens having a fixed elevation focus with the orthogonally disposed 1-D arrays.

29. The method of claim 28, wherein the lens is a physical lens.

30. The method of claim 29, wherein the lens is an electronic lens.

31. The method of claim 28, further comprising:
providing two-way focusing in a plane of the orthogonally disposed 1-D arrays.

32. An ultrasound imaging system, comprising:
a pair of 1-D arrays oriented orthogonal to each other and row-column addressed; and
processing components that process an output of the pair of 1-D arrays to estimate an axial and two lateral components using 2-D velocity vector estimator.

* * * * *